United States Patent
Henderson et al.

(10) Patent No.: US 10,279,127 B2
(45) Date of Patent: May 7, 2019

(54) MEDICAMENT DELIVERY DEVICE WITH ALIGNMENT MECHANISM

(71) Applicant: SANOFI-AVENTIS DEUTSCHLAND GMBH, Frankfurt am Main (DE)

(72) Inventors: Charley Henderson, Cambridgeshire (GB); David Cross, Hertfordshire (GB); Douglas Ivan Jennings, Hertfordshire (GB); Ryan Anthony McGinley, Cambridgeshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 43 days.

(21) Appl. No.: 14/423,737

(22) PCT Filed: Sep. 3, 2013

(86) PCT No.: PCT/EP2013/068133
§ 371 (c)(1),
(2) Date: Feb. 25, 2015

(87) PCT Pub. No.: WO2014/037322
PCT Pub. Date: Mar. 13, 2014

(65) Prior Publication Data
US 2015/0217063 A1  Aug. 6, 2015

(30) Foreign Application Priority Data
Sep. 4, 2012 (EP) .................... 12182907

(51) Int. Cl.
*A61M 5/00* (2006.01)
*A61M 5/46* (2006.01)

(52) U.S. Cl.
CPC ....... *A61M 5/46* (2013.01); *F04C 2270/0421* (2013.01)

(58) Field of Classification Search
CPC .......... A61M 2005/206; A61M 5/2033; A61M 5/326; A61M 5/3202; A61M 5/3287;
(Continued)

(56) References Cited

U.S. PATENT DOCUMENTS

| | | | | |
|---|---|---|---|---|
| 4,826,490 A | * | 5/1989 | Byrne et al. | 604/198 |
| 4,894,055 A | * | 1/1990 | Sudnak | 604/198 |

(Continued)

FOREIGN PATENT DOCUMENTS

| | | |
|---|---|---|
| EP | 2415493 | 2/2012 |
| JP | K2005-521537 | 7/2005 |

(Continued)

OTHER PUBLICATIONS

International Search Report for Int. App. No. PCT/EP2013/068133, completed Sep. 24, 2013.
(Continued)

*Primary Examiner* — Scott J Medway
(74) *Attorney, Agent, or Firm* — Fish & Richardson P.C.

(57) ABSTRACT

Described is a medicament delivery device having a case and a plurality of projections movable relative to the case between an extended position in which distal ends of the projections extends beyond a distal face of the case and a refracted position in which the distal ends of the projections are substantially co-planar with the distal face.

18 Claims, 3 Drawing Sheets

(58) Field of Classification Search
CPC .......... A61M 2205/581; A61M 5/3157; A61M 5/321; A61M 5/14248; A61M 2005/14252; A61M 2005/14268; A61M 5/158; A61M 25/02
See application file for complete search history.

(56) References Cited

U.S. PATENT DOCUMENTS

| | | | | |
|---|---|---|---|---|
| 4,986,819 | A * | 1/1991 | Sobel | 604/198 |
| 5,411,487 | A * | 5/1995 | Castagna | A61M 5/3271 604/198 |
| 5,593,387 | A * | 1/1997 | Rupp | A61M 5/3216 604/110 |
| 6,080,135 | A * | 6/2000 | Van Stokkum | A61M 5/3257 604/192 |
| 6,569,124 | B1 * | 5/2003 | Perouse | A61M 5/3257 604/110 |
| 7,544,185 | B2 * | 6/2009 | Bengtsson | 604/173 |
| 7,604,647 | B2 * | 10/2009 | Chen | 606/166 |
| 8,235,950 | B2 * | 8/2012 | Emmott et al. | 604/192 |
| 8,708,968 | B2 * | 4/2014 | Julian et al. | 604/192 |
| 9,078,978 | B2 * | 7/2015 | Schraga | |
| 9,125,985 | B2 * | 9/2015 | Adams | A61M 5/50 |
| 2002/0020646 | A1 * | 2/2002 | Groth et al. | 206/366 |
| 2002/0193746 | A1 * | 12/2002 | Chevallier | A61M 5/326 604/197 |
| 2003/0004465 | A1 * | 1/2003 | Ferguson et al. | 604/198 |
| 2003/0168366 | A1 * | 9/2003 | Hirsiger | A61M 5/326 206/365 |
| 2003/0191438 | A1 | 10/2003 | Ferguson et al. | |
| 2003/0212362 | A1 | 11/2003 | Roser | |
| 2004/0236284 | A1 * | 11/2004 | Hoste et al. | 604/198 |
| 2006/0135908 | A1 * | 6/2006 | Liniger et al. | 604/93.01 |
| 2009/0043265 | A1 | 2/2009 | Schneider | |
| 2009/0171311 | A1 * | 7/2009 | Genosar et al. | 604/411 |
| 2009/0216215 | A1 * | 8/2009 | Thalmann et al. | 604/506 |
| 2010/0049125 | A1 * | 2/2010 | James et al. | 604/110 |
| 2011/0054411 | A1 * | 3/2011 | Dowds et al. | 604/198 |
| 2011/0092915 | A1 * | 4/2011 | Olson et al. | 604/198 |
| 2012/0046615 | A1 | 2/2012 | Koiwai et al. | |
| 2012/0123346 | A1 * | 5/2012 | Davies et al. | 604/191 |
| 2013/0253430 | A1 * | 9/2013 | Kouyoumjian et al. | 604/151 |

FOREIGN PATENT DOCUMENTS

| | | |
|---|---|---|
| JP | K2007-502156 | 2/2007 |
| JP | K2010-501211 | 1/2010 |
| JP | K2011-235108 | 11/2011 |
| WO | WO 01/91837 | 12/2001 |
| WO | WO 2005/018722 | 3/2005 |
| WO | WO 2010/116832 | 10/2010 |

OTHER PUBLICATIONS

International Preliminary Report on Patentability in International Application No. PCT/EP2013/068133, dated Mar. 10, 2015, 5 pages.

* cited by examiner

MEDICAMENT DELIVERY DEVICE WITH ALIGNMENT MECHANISM

CROSS REFERENCE TO RELATED APPLICATIONS

The present application is a U.S. National Phase Application pursuant to 35 U.S.C. § 371 of International Application No. PCT/EP2013/068133 filed Sep. 3, 2013, which claims priority to European Patent Application No. 12182907.1 filed Sep. 4, 2012. The entire disclosure contents of these applications are herewith incorporated by reference into the present application.

TECHNICAL FIELD

The invention relates to a medicament delivery device with an alignment mechanism.

BACKGROUND

Administering an injection is a process which presents a number of risks and challenges for users and healthcare professionals, both mental and physical. Injection devices typically fall into two categories—manual devices and auto-injectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Conventional injection devices do not provide any alignment mechanisms, which can lead to incorrect delivery depth (e.g., intradermal when it should have been subcutaneous) and incorrect dosing (e.g., if the medicament is delivered to an incorrect depth). Further, it is very difficult for a user to determine whether a conventional injection device is properly aligned since there is generally no feedback about alignment, and the user is required to visually approximate the orientation of the injection device relative to the injection site.

Thus, there remains a need for an improved medicament delivery device with an alignment mechanism.

SUMMARY

It is an object of the present invention to provide an improved medicament delivery device with an alignment mechanism.

In an exemplary embodiment, a medicament delivery device according to the present invention comprises a case and a plurality of projections movable relative to the case between an extended position in which distal ends of the projections extends beyond a distal face of the case and a retracted position in which the distal ends of the projections are substantially co-planar with the distal face. Each of the projections is biased by a spring toward the extended position. Each of the projections are biased by a different spring.

In an exemplary embodiment, the plurality of projections are symmetrically spaced.

In an exemplary embodiment, the plurality of projections includes three projections spaced 120° relative to each other.

In an exemplary embodiment, the medicament delivery device further comprises a trigger button, and a locking mechanism operably coupled to the trigger button and the plurality of projections. The locking mechanism locks the trigger button when at least one of the projections is not in the retracted position. The locking mechanism unlocks the trigger button when the projections are in the retracted position.

In an exemplary embodiment, the medicament delivery device further comprises an indicator displaying a first indicia when at least one of the projections is not in the retracted position and a second indicia when the projections are in the retracted position. The first indicia is a first color and the second indicia is a second color.

In an exemplary embodiment, an audible feedback is generated when the projections are in the retracted position.

In an exemplary embodiment, the projections are disposed in an alignment mechanism removably coupled to the case.

In an exemplary embodiment, when at least one of the projections returns to the extended position after all of the projections were in the retracted position, at least one of a safety mechanism, a dose control mechanism and a needle retraction mechanism is activated.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(w-carboxyheptadecanoyl)-des(B30) human insulin and B29-N-(ωcarboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4derivative;
or an Exendin-4derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
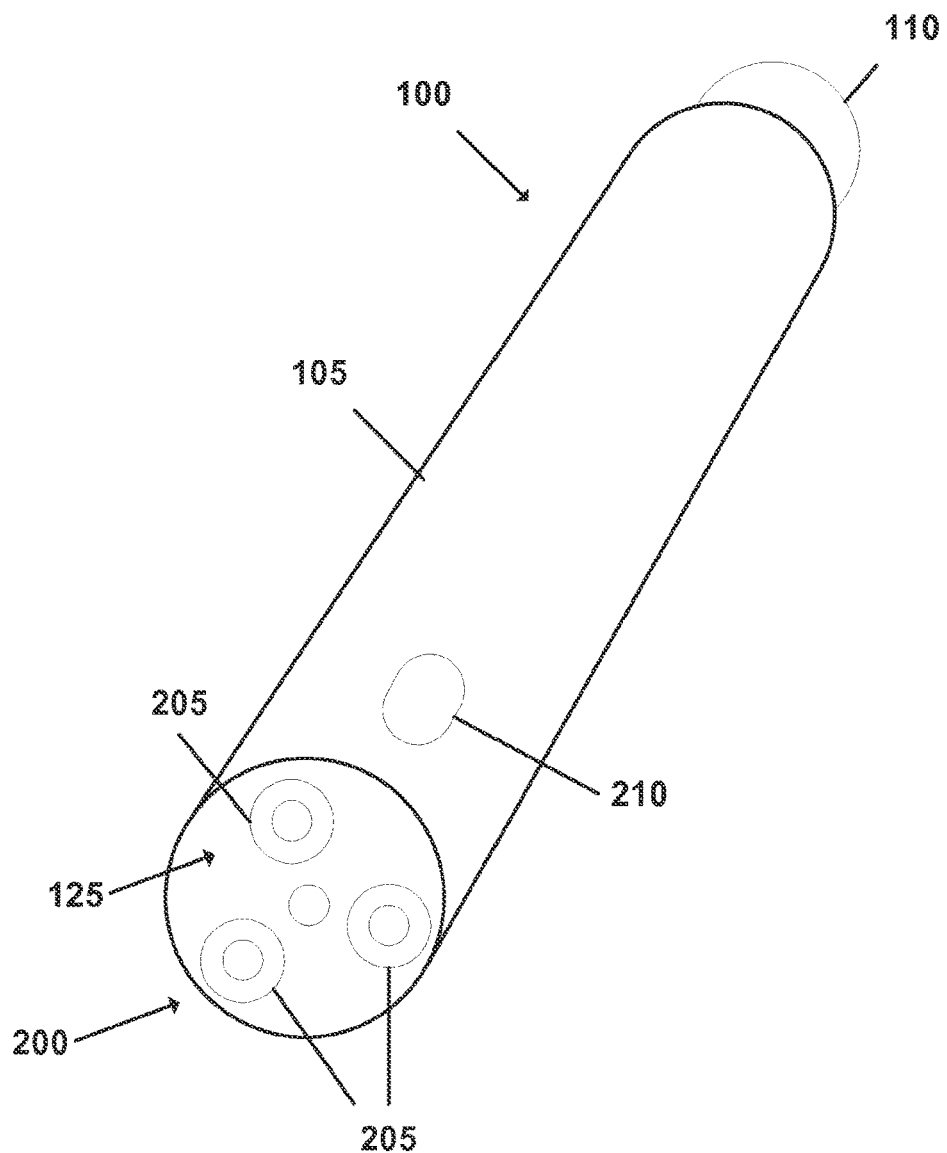
FIG. 1 shows an exemplary embodiment of a medicament delivery device with an alignment mechanism according to the present invention.

FIG. 1 shows an exemplary embodiment of a medicament delivery device 100 with an alignment mechanism 200 according to the present invention. The delivery device 100 may be any type of injection device which is used to inject a medicament from a syringe or cartridge. Those of skill in the art will understand that such injection devices include, but are not limited to, pen injectors, pre-filled syringes, autoinjectors, perfusion devices, infusion devices, etc.

In an exemplary embodiment, the alignment mechanism 200 is integrally formed with the delivery device 100. In another exemplary embodiment, the alignment mechanism 200 may be an attachment to a pre-existing delivery device. For example, the alignment mechanism 200 may be a cap-type attachment which is removably coupled to the delivery device 100 and can be reused.

In the exemplary embodiment, the delivery device 100 may include components common to conventional delivery devices such as, for example, a case, 105, one or more springs, plungers, needle shields, syringe/cartridge, syringe/cartridge carriers, trigger button 110, etc.

In the exemplary embodiment, an alignment mechanism 200 is disposed on a distal end of the delivery device 100. The alignment mechanism 200 may prevent actuation of the delivery device 100 until the delivery device 100 has been pressed against and properly aligned relative to an injection site. For example, for many uses, proper alignment of the delivery device 100 will be perpendicular to the injection site; however, in other uses, other angles of alignment may be utilized.

In an exemplary embodiment, the alignment mechanism 200 includes a plurality of individually movable projections 205 having an extended position in which distal ends of the projections 205 extend beyond a distal face 125 of the case 105 and a retracted position in which the distal ends of the projections 205 are substantially co-planar with the distal face. The projections 205 may be biased in the extended position by springs (not shown) or other resilient elements. In an exemplary embodiment, the projections 205 are spaced symmetrically about a longitudinal axis of the delivery device 100 on the distal face of the case 105. For example, the exemplary embodiment shown in FIG. 1 includes three projections 205 spaced 120° from each other.

The projections 205 may be operably coupled to a locking mechanism that is adapted to lock and unlock the trigger button 110. For example, when the projections 205 are in the extended position, the locking mechanism may lock the trigger button 110, to prevent actuation during improper positioning and alignment of the delivery device 100. For the locking mechanism to unlock the trigger button 110, all of the projections 205 must be in the retracted position.

In an exemplary embodiment, the locking mechanism is mechanical. For example, when the projections 205 are all in the retracted position, the locking mechanism may be disengaged from the trigger button 110. When the projections 205 are not all in the retracted position, the locking mechanism may engage the trigger button 110 and prevent its actuation. In another exemplary embodiment, the projections 205 may be coupled to a sensor which emits a signal when all of the projections 205 are in the retracted position, and a controller utilizes the signal to disengage the locking mechanism from the trigger button 110.

In an exemplary embodiment, an indicator window 210 may be disposed on the delivery device 100. The indicator window 210 may provide visual indicator as feedback regarding the alignment of the delivery device 100 relative to the injection site. For example, the visual indicator may be red until all of the projections 205 are in the retracted position, and the visual indicator may then display green, signalling to the user that the trigger button 110 is unlocked. Those of skill in the art will understand that various visual indicators, including color, may be used, e.g., text ("locked"/ "unlocked"), graphic indicia (an "X" and a check mark), etc.

In another exemplary embodiment, an audible feedback (e.g., a "click") may be generated when all of the projections 205 are in the retracted position.

Figure 2:
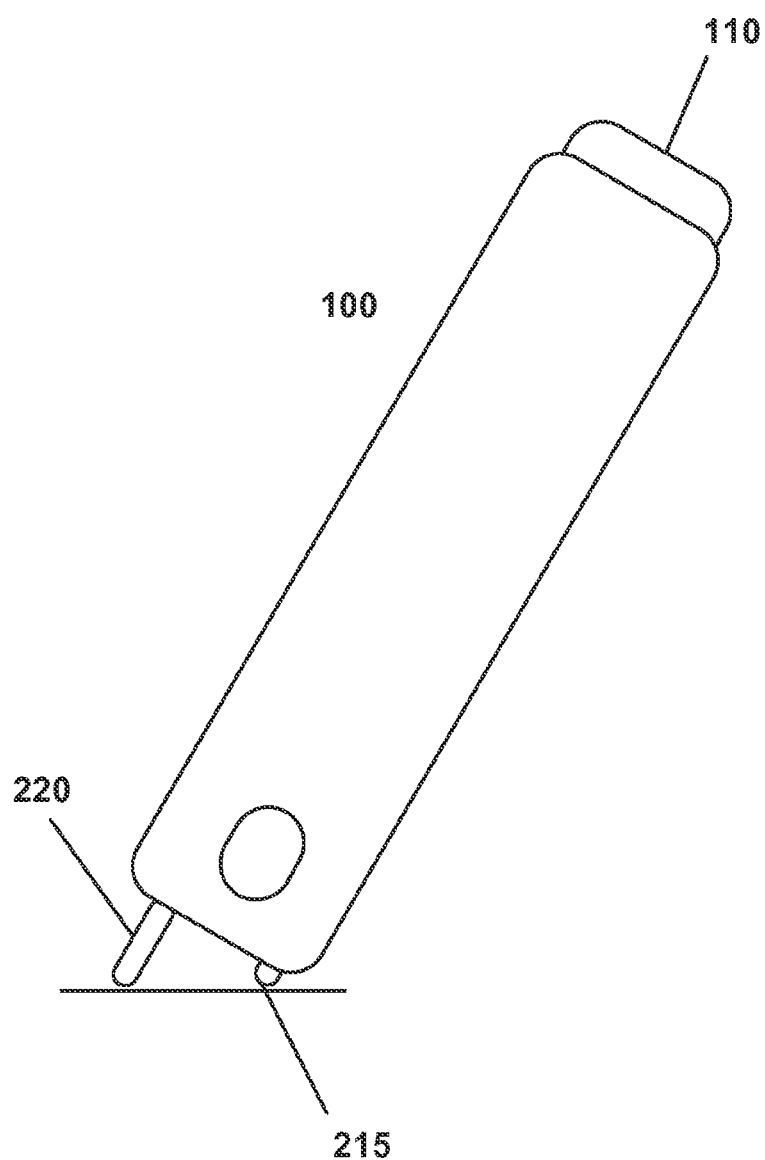
FIG. 2 shows an exemplary embodiment of a medicament delivery device with an alignment mechanism during use according to the present invention.

FIG. 2 shows an exemplary embodiment of a medicament delivery device 100 having an alignment mechanism 100 during use. In the exemplary embodiment shown in FIG. 2, the delivery device 100 is being placed against the injection site at a non-perpendicular angle. As shown, a first projection 215 has achieved the retracted position; however a second projection 220 remains in the extended position. Because the first and second projections 215, 220 have not achieved the retracted position, the locking mechanism may remain engaged to the trigger button 110 and prevent actuation of the trigger button 110.

Figure 3:
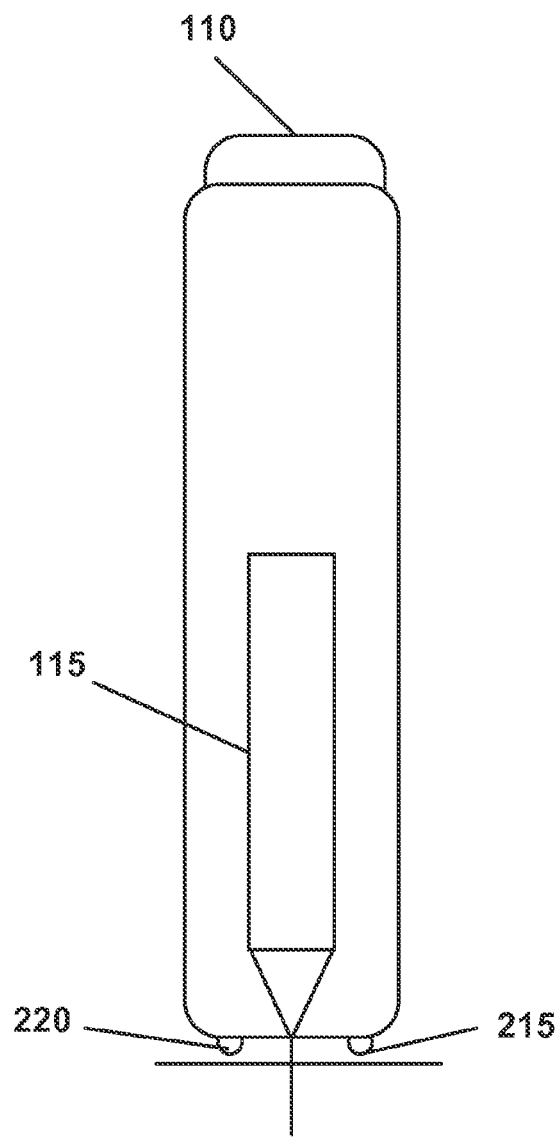
FIG. 3 shows an exemplary embodiment of a medicament delivery device with an alignment mechanism during use according to the present invention.

FIG. 3 shows an exemplary embodiment of a medicament delivery device 100 having an alignment mechanism 100 during use. In the exemplary embodiment shown in FIG. 3, the delivery device 100 is being placed against the injection site at a perpendicular angle, which is the proper orientation/ alignment of the delivery device 100 relative to the injection site. As shown, the first projection 215 and the second projections 220 have achieved the retracted position, e.g., by being pushed against the injection site. Because the first and second projections 215, 220 have achieved the retracted position, the locking mechanism disengages the trigger button 110 and allows actuation of the trigger button 110.

FIG. 3 shows that, after actuation of the trigger button 110, a dose of medicament may be delivered by a syringe 115 or a cartridge.

In an exemplary embodiment, the alignment mechanism 200 may further be used as a safety and/or dose control mechanism. For example, if, after the trigger button 110 is actuated, the delivery device 100 becomes mis-aligned relative to the injection site, at least one of the projections 205 may return to the extended position. At that point or, in another example when the delivery device 100 is removed from the injection site after an injection, a safety mechanism (e.g., needle shield deployment or syringe withdrawal into the case 105), a dose control mechanism (e.g., stopping advancement of a plunger into the syringe 115) and/or a needle retraction mechanism may be activated.

In an exemplary embodiment, the alignment mechanism 200 may further be utilized to ensure a substantially planar injection site. For example, if the intended injection site has scar tissue or a non-uniform surface, at least one of the projections 205 may not achieve the retracted position, and thus the trigger button 110 may remain locked.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medicament delivery device, comprising:
   a case configured to contain a syringe or cartridge having a needle, the needle being configured to extend through a geometric center of a distal face of the case;
   a trigger button;
   a plurality of projections movable relative to the case between an extended position in which distal ends of the projections extend beyond the distal face of the case and a retracted position in which the distal ends of the projections are substantially co-planar with the distal face, each projection being offset from the geometric center of the distal face; and
   a locking mechanism operably coupled to the trigger button and the plurality of projections, wherein the locking mechanism locks the trigger button when at least one of the projections is not in the retracted position,
   wherein each projection is extendable and retractable independently of other projections of the plurality of projections, and
   wherein the projections are disposed in an alignment mechanism removably coupled to the case.

2. The medicament delivery device according to claim 1, wherein each of the projections is biased by a spring toward the extended position.

3. The medicament delivery device according to claim 2, wherein each of the projections are biased by a different spring.

4. The medicament delivery device of claim 1, wherein the plurality of projections are symmetrically spaced.

5. The medicament delivery device of claim 1, wherein the plurality of projections includes three projections spaced 120° relative to each other.

6. The medicament delivery device according to claim 1, wherein the locking mechanism unlocks the trigger button when the projections are in the retracted position.

7. The medicament delivery device of claim 1, further comprising:
an indicator displaying a first indicia when at least one of the projections is not in the retracted position and a second indicia when the projections are in the retracted position.

8. The medicament delivery device according to claim 7, wherein the first indicia is a first color and the second indicia is a second color.

9. The medicament delivery device of claim 1, wherein an audible feedback is generated when the projections are in the retracted position.

10. The medicament delivery device of claim 1, wherein when at least one of the projections returns to the extended position after all of the projections were in the retracted position, at least one of a safety mechanism, a dose control mechanism and a needle retraction mechanism is activated.

11. A medicament delivery device, comprising:
a case configured to contain a syringe or cartridge having a needle, the needle being configured to extend through a geometric center of a distal face of the case;
a plurality of projections moveable relative to the case between an extended position in which distal ends of the projections extend beyond the distal end face of the case and a retracted position in which the distal ends of the projections are substantially co-planar with the distal end face, each projection being offset from the geometric center of the distal face; and
wherein the plurality of projections are distributed around a needle opening provided in the distal end face of the case,
wherein each projection is extendable and retractable independently of other projections of the plurality of projections;.
wherein each of the projections is biased by a spring toward the extended position, and
wherein each of the projections is biased by a different spring.

12. The medicament delivery device of claim 11, wherein the plurality of projections are symmetrically spaced.

13. A medicament delivery device, comprising:
a case configured to contain a syringe or cartridge having a needle, the needle being configured to extend through a geometric center of a distal face of the case;
a plurality of projections moveable relative to the case between an extended position in which distal ends of the projections extend beyond the distal end face of the case and a retracted position in which the distal ends of the projections are substantially co-planar with the distal end face, each projection being offset from the geometric center of the distal face,
wherein the plurality of projections are distributed around a needle opening provided in the distal end face of the case,
wherein each projection is extendable and retractable independently of other projections of the plurality of projections, and
wherein the plurality of projections includes three projections spaced 120° relative to each other.

14. The medicament delivery device of claim 11, further comprising:
a trigger button; and
a locking mechanism operably coupled to the trigger button and the plurality of projections, wherein the locking mechanism locks the trigger button when at least one of the projections is not in the retracted position.

15. The medicament delivery device according to claim 14, wherein the locking mechanism unlocks the trigger button when the projections are in the retracted position.

16. The medicament delivery device of claim 11, further comprising:
an indicator displaying a first indicia when at least one of the projections is not in the retracted position and a second indicia when the projections are in the retracted position.

17. The medicament delivery device according to claim 16, wherein the first indicia is a first color and the second indicia is a second color.

18. The medicament delivery device of claim 1, wherein the plurality of projections project through the distal face of the case.

* * * * *

UNITED STATES PATENT AND TRADEMARK OFFICE
CERTIFICATE OF CORRECTION

PATENT NO. : 10,279,127 B2  
APPLICATION NO. : 14/423737  
DATED : May 7, 2019  
INVENTOR(S) : Charley Henderson et al.

Page 1 of 1

It is certified that error appears in the above-identified patent and that said Letters Patent is hereby corrected as shown below:

In the Claims

In Column 9, Line 37, in Claim 11, delete "projections;." and insert -- projections, --

Signed and Sealed this  
Thirtieth Day of July, 2019

Andrei Iancu  
*Director of the United States Patent and Trademark Office*